US00PP32525P2

(12) United States Plant Patent
Cherry

(10) Patent No.: US PP32,525 P2
(45) Date of Patent: Nov. 24, 2020

(54) ***CUPHEA* PLANT NAMED 'CUPP1751'**

(50) Latin Name: *Cuphea ignea*
Varietal Denomination: CUPP1751

(71) Applicant: Robert Cherry, Gawler (AU)

(72) Inventor: Robert Cherry, Gawler (AU)

( * ) Notice: Subject to any disclaimer, the term of this patent is extended or adjusted under 35 U.S.C. 154(b) by 0 days.

(21) Appl. No.: 16/887,089

(22) Filed: May 29, 2020

(51) Int. Cl.
*A01H 5/02* (2018.01)
*A01H 6/00* (2018.01)

(52) U.S. Cl.
USPC ..... Plt./420

(58) Field of Classification Search
USPC ..... Plt./420
See application file for complete search history.

*Primary Examiner* — Susan McCormick Ewoldt
(74) *Attorney, Agent, or Firm* — Barbara Campbell; Weatherly IP Solutions, LLC

(57) ABSTRACT

A new and distinct cultivar of *Cuphea* named 'CUPP1751' that is characterized by prolifically self-branching dense and compact mounding plant habit, bi-colored bright vermillion-red and lemon-yellow tubular flowers which are borne in great profusion. In combination, these characteristics set 'CUPP1751' apart from all other existing varieties of *Cuphea* known to the inventor.

2 Drawing Sheets

Genus and species: *Cuphea ignea.*
Variety denomination: 'CUPP1751'.

BACKGROUND

The present invention relates to a new and distinct cultivar of *Cuphea* grown as an ornamental plant for use in the garden, in planted containers and in the landscape. The new variety from the family Lythraceae is known botanically as *Cuphea hybrida* and is commonly termed the cigar plant. The new invention will be referred to hereinafter by the variety name 'CUPP1751'.

In 2007, the inventor began to assemble at his nursery in Kulnura, New South Wales, Australia a collection of species and seedlings of various *Cuphea* plants including unnamed plants and seedlings of *Cuphea cyanea* and *Cuphea ignea*. The plants in the collection were exposed to open-pollination and further plants were raised from collected seed. In 2014, the inventor observed that one such seedling grew with a compact highly self-branching dome-shaped habit, and bore brightly bi-colored tubular flowers in great profusion. The inventor isolated and named this seedling as 'CUPP1751'. The parents of 'CUPP1751' were unnamed and cannot be identified.

The distinguishing characteristics of 'CUPP1751' include prolific self-branching leading to a dense mounding plant habit, and the production of self-cleaning tubular bi-colored flowers in great profusion.

The inventor carried out the first asexual propagation in 2015, using vegetative tip cuttings in Kulnura, New South Wales, Australia. The inventor has since determined that 'CUPP1751' is stable and reproduces true-to-type in successive generations of asexual propagation via vegetative tip cuttings.

SUMMARY

The following traits have been repeatedly observed and represent the distinguishing characteristics of the new

*Cuphea* variety named 'CUPP1751'. These traits in combination set 'CUPP1751' apart from all other existing varieties of *Cuphea* known to the inventor. 'CUPP1751' has not been tested under all possible conditions and phenotypic differences may be observed with variations in environmental, climatic, and cultural conditions without however any variance in genotype.

1. 'CUPP1751' is prolifically self-branching and forms a dense and compact mounding plant habit.
2. 'CUPP1751' bears tubular flowers at each node and in great profusion year-round.
3. The flowers of 'CUPP1751' are bicolored, being bright vermillion red towards the base and bright yellow towards the apex.
4. The flowers of 'CUPP1751' are self-cleaning, falling off the plant while still colorful. In consequence, plants of 'CUPP1751' bear only fresh and brightly colored flowers.
5. 'CUPP1751' grows rapidly. After 15 weeks from planting a rooted cutting into a 2-gallon container, 'CUPP1751' achieves a height of 30 cm and a spread of 60 cm to 75 cm.
6. When fully established in the landscape, 'CUPP1751' achieves a height of 60 cm and a spread of 90 cm to 100 cm.
7. 'CUPP1751' is hardy to USDA Zone 10.

DESCRIPTION OF THE DRAWINGS

The accompanying color photographs illustrate the overall appearance of the new *Cuphea* variety named 'CUPP1751' showing the color as true as is reasonably possible to obtain in color reproductions of this type. Color in the photographs may differ from color values cited in the detailed botanical description, which accurately describe the actual color of the new variety 'CUPP1751'. Each photograph is taken from a one-year-old plant of 'CUPP1751' which had been grown outdoors in Oxnard, Calif. The photographs were made using conventional digital photographic techniques and although flower and foliage color may appear different from actual color due to light reflectance, they are as accurate as possible by such photography.

DESCRIPTION OF THE NEW VARIETY

Figure 1:
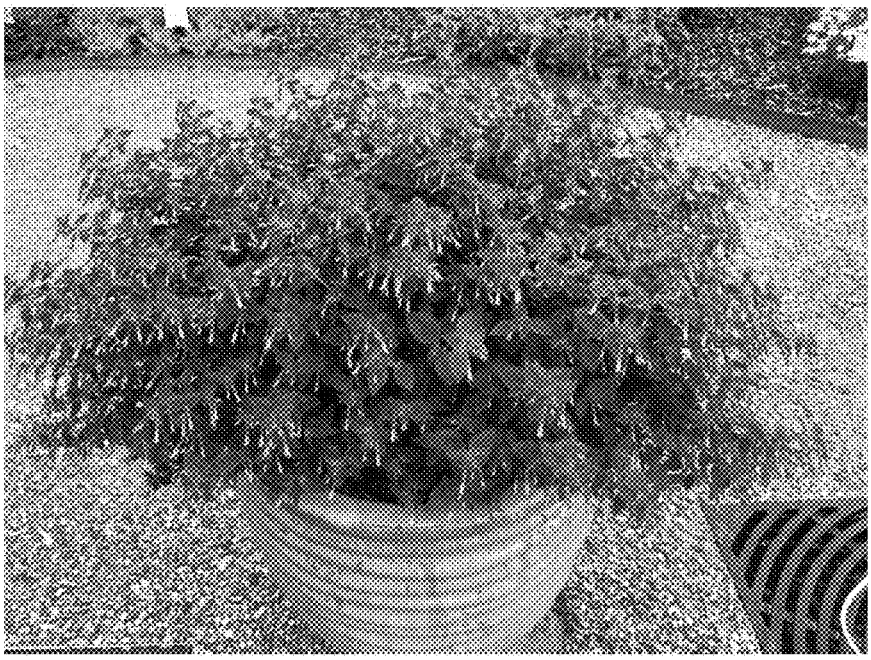
FIG. 1 shows a plant of 'CUPP1751' growing in a container.
Figure 2:
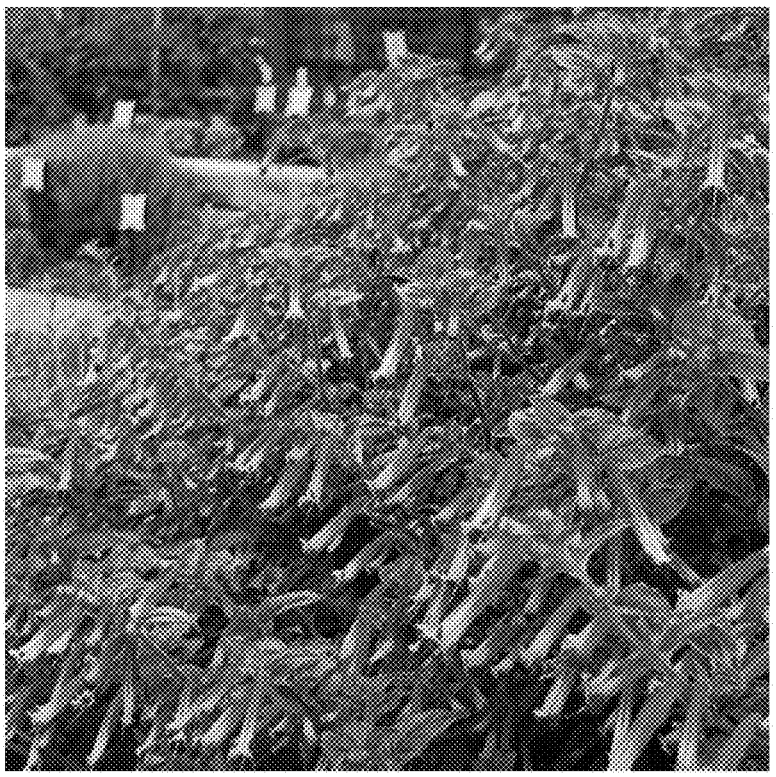
FIG. 2 shows a close-up view of 'CUPP1751' from FIG. 1.
Figure 3:
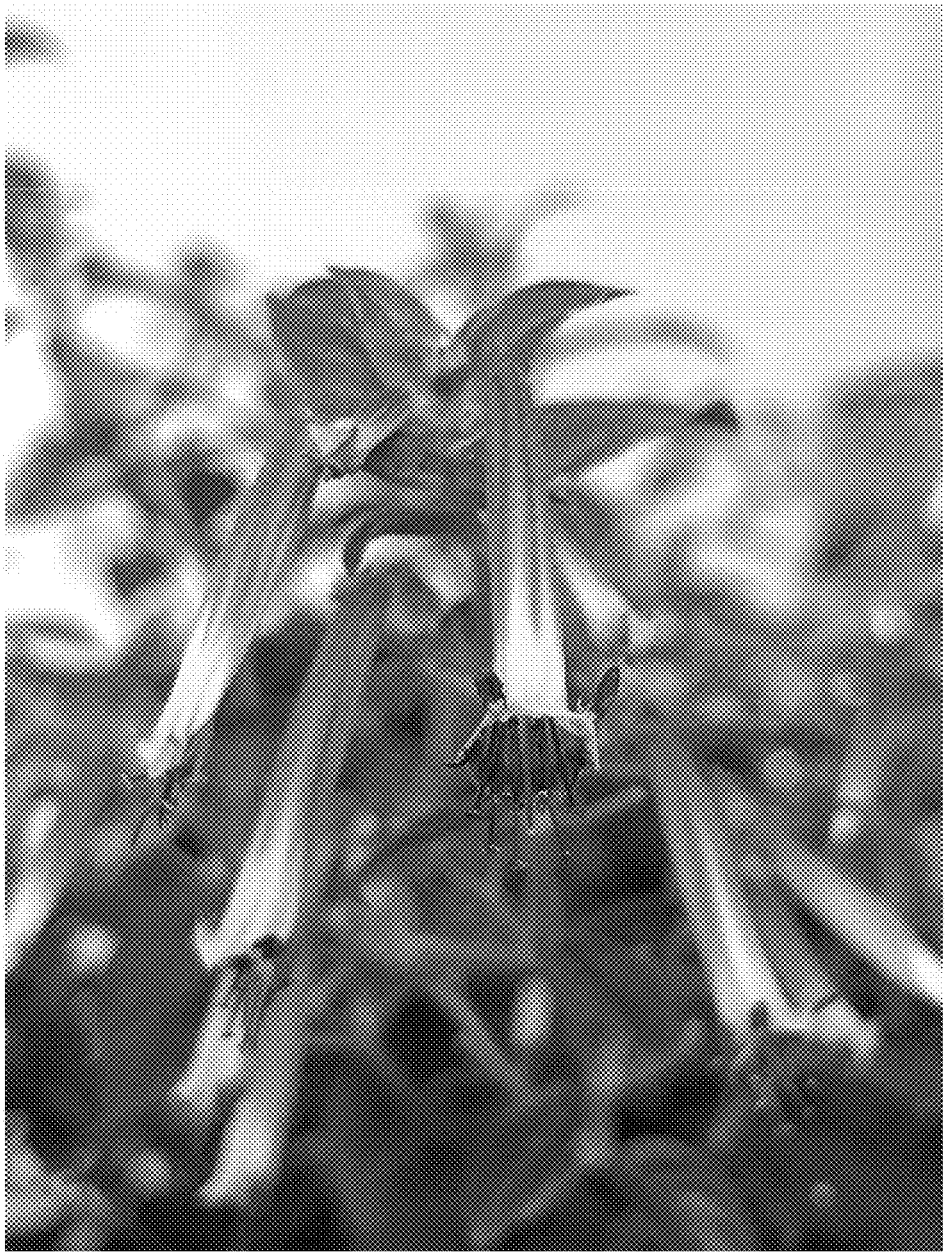
FIG. 3 shows a close-up view of the bicolored tubular flowers of 'CUPP1751' with its set of stamens and depicting the purple ear-like rudimentary pair of petals.

The following is a detailed botanical description of the new *Cuphea* variety named 'CUPP1751'. Observations, measurements, values and comparisons were collected in Santa Barbara, Calif., from 9-month-old plants grown outdoors. Color determinations are made in accordance with the Fifth Edition (2007) of The Royal Horticultural Society Colour Chart from London, England, except where general color terms of ordinary dictionary significance are used.

Botanical classification: *Cuphea* x *hybrida* 'CUPP1751'.

*Family*.—Lythraceae.

*Genus*.—*Cuphea*.

*Species*.—X *hybrida*.

*Denomination*.—'CUPP1751'.

*Common name*.—Cigar plant.

Parentage: *Cuphea* x *hybrida* 'CUPP1751' is a hybrid resulting from the open pollination of the following species: *Cuphea cyanea, Cuphea ignea*.

Plant:

*Habit*.—Dense, compact, mounding.

*Commercial category*.—Ornamental.

*Use*.—For garden and landscape.

*Suggested commercial container size*.—1 gallon or 2-gallon container.

*Propagation method*.—Vegetative cuttings.

*Rooting system*.—Fine.

*Vigor*.—Highly vigorous and naturally self-branching.

*Crop time*.—4 months to produce a 2-gallon container from taking an initial cutting.

*Plant dimensions*.—After 15 weeks from planting a rooted cutting into a 2-gallon container, 'CUPP1751' achieves a height of 20 cm and a spread of 60 cm to 75 cm. When fully established in the landscape, 'CUPP1751' achieves a height of 60 cm and a spread of 90 cm to 100 cm. in width.

*Cultural requirements*.—Grow in full sun to part shade, regular soil, with regular water.

*Pest or disease resistance*.—None known to the inventor.

*Pest or disease susceptibility*.—None known to the inventor.

*Hardiness*.—USDA Zone 10.

*Special considerations*.—Blooms continually throughout the year in USDA Zone 10.

Stem (main stem, primary branches, secondary branches):

*Main stem* (*below pinch at* 8 *cm*.).—Shape: Cylindrical. Dimensions: 8 cm in length, 0.5 cm in diameter at soil level. Surface: Rough. Color between N199B and N200A.

*Primary branches*.—Shape: Cylindrical. Dimensions: 25 cm to 30 cm in length, 2-3 mm in diameter. Internode distance: 2.0 cm to 2.5 cm. Surface: Lightly pubescent becoming smooth, glabrous with age. Color: 61A.

*Secondary branches*.—Shape: Cylindrical. Dimensions: 3 cm to 5 cm in length, 1.5 mm in diameter at soil level. Internode distance: 1.0 cm to 1.5 cm. Surface: Lightly pubescent becoming smooth, glabrous with age. Color: 61A except final one or two nodes 145B. Branch quantity: Very numerous, approximately 50 to 75 primary and secondary branches.

Foliage:

*Type*.—Evergreen.

*Leaf arrangement*.—Opposite.

*Leaf division*.—Simple.

*Leaf margin*.—Entire, ciliate. Very fine silver-grey hairs, less than 0.5 mm in length.

*Leaf surface* (*abaxial and adaxial*).—Glabrous.

*Leaf shape*.—Lanceolate.

*Leaf length*.—2.5 cm to 3.5 cm.

*Leaf width*.—1.5 cm to 2.0 cm.

*Leaf color* (*adaxial surface*).—137B.

*Leaf color* (*abaxial surface*).—191B.

*Leaf apex*.—Acute.

*Leaf base*.—Attenuate.

*Venation*.—Pinnate.

*Vein color* (*adaxial surface*).—As leaf, 137B. Evident only as depressions.

*Vein color* (*abaxial surface*).—137B, slightly raised.

*Attachment*.—Petiolate.

*Petiole shape*.—sub-cylindrical.

*Petiole surface*.—Puberulent.

*Petiole color*.—191B.

*Petiole dimensions*.—1.0 mm to 1.5 mm length, 1 mm in width.

*Leaf fragrance*.—None observed.

Inflorescence:

*Inflorescence* (*axillary and terminal*).—Solitary flower.

*Inflorescence structure*.—Modified calyx whose sepals are completely fused into a colorful floral tube which acts as pollinator attractant. Where present, tiny petals attached to apex of floral tube as a pair of prominent ear-like appendages held uppermost above the flower tube apex.

*Inflorescence shape*.—Tubular with six longitudinal ribs. Tube widening towards apex. Tube terminates at base with downward-facing nectar sac.

*Inflorescence aspect*.—Downward, approximately 45 degrees below the horizontal.

*Inflorescence quantity*.—Very numerous, typically 10 to 15 flowers per stem, approximately 500 flowers per plant at any one time.

*Blooming season*.—Year-round if frost-free and unshaded.

*Inflorescence dimensions*.—2.5 cm in length, 3 mm in diameter at base, 5 mm in diameter at apex.

*Inflorescence color* (*adaxial surface*).—Nectar sac and approximately two-thirds of entire tube length from base, 50A; approximately one-third of length from tube apex, 13C. These two colored surfaces, 50A and 13C, extend longitudinally towards apex and base respectively.

*Inflorescence color* (*abaxial surface*).—13C, except 64B for nearest 5 mm of inside surface to tube apex.

This purple color 64B stops abruptly at 5 mm from apex after which the inside surface becomes 13C.

*Inflorescence surface*.—Glabrous.

*Inflorescence apex* (*bears petal pair*).—

*Color at rim*.—13C.

*Rim surface*.—Ciliate, fine silver-grey hairs 0.5 mm to 1 mm in length. Clear glandular secretions evident on some hairs.

*Petals*.—2, cupped, ear-like, positioned superior to apex and held nearly vertical.

*Distance between petals*.—4 mm.

*Petal shape, dimensions, surface*.—Rhombic-ovoid, 2.5 mm to 3.0 mm in length, 1.5 mm in width. Surface, glabrous.

*Petal color*.—Both surfaces, 62B.

*Persistent or self-cleaning*.—Self-cleaning.

*Peduncle color*.—145C.

*Peduncle dimensions*.—8 mm to 11 mm in length, 1 mm. in diameter.

*Peduncle shape*.—Cylindrical.

*Peduncle surface*.—Pubescent.

*Inflorescence fragrance*.—None observed.

*Lastingness of inflorescence* (*range*).—3 to 5 days.

Reproductive organs:

*Stamens*.—Quantity: 10 adnate to floral tube. Length: Ranges between 3 mm (stamens entirely inside floral tube) and 11 mm (stamens strongly exerted above floral tube apex). Diameter: 1 mm. Color: 71A. Anthers: Ovoid, dorsifixed, 2 mm in length, 1 mm in width, color N77D. Pollen: None observed.

*Pistil quantity*.—1.

*Pistil dimensions*.—2.5 cm in length, 1 mm in diameter.

*Pistil color*.—157D becoming 71A towards and immediately beneath stigma.

*Stigma*.—Miniscule, hemispherical, diameter very slightly greater than diameter of pistil at attachment.

*Stigma color*.—156D.

*Ovary position*.—Superior.

*Ovary shape*.—Ovoid.

*Ovary dimensions*.—1.5 mm in height, 2 mm in diameter.

*Ovary color* (*observed immature*).—145B.

COMPARISON WITH KNOWN VARIETY

The variety of *Cuphea* which the inventor considers most closely to resemble 'CUPP1751' is *Cuphea* 'Pink Mouse' (unpatented). Both varieties 'CUPP1751' and 'Pink Mouse' bear bicolored tubular flowers with tiny ear-like petal appendages at the rim of the floral tube. Whereas the tube of 'Pink Mouse' is bicolored soft pink and lemon yellow, the flowers of 'CUPP1751' are bicolored vermillion red and deeper yellow in color. Whereas the petal appendages of 'Pink Mouse' are very dark purple in color, those of 'CUPP1751' are lighter purple in color.

I claim:

1. A new and distinct variety of *Cuphea* plant named 'CUPP1751' as described and illustrated herein.

* * * * *